United States Patent [19]

Elliott et al.

[11] 4,127,493
[45] Nov. 28, 1978

[54] POLYESTER LUBRICANT ADDITIVES, THEIR PREPARATION AND COMPOSITIONS CONTAINING THEM

[75] Inventors: John S. Elliott, Beaconsfield, England; Bryan T. Davis, West Bloomfield, Mich.; Stephen Norman, St. Louis, Mo.

[73] Assignee: Ethyl Corporation, Richmond, Va.

[21] Appl. No.: 854,327

[22] Filed: Nov. 23, 1977

Related U.S. Application Data

[62] Division of Ser. No. 506,910, Sep. 17, 1974, Pat. No. 4,070,370.

[30] Foreign Application Priority Data

Sep. 18, 1973 [GB] United Kingdom ............... 43735/73

[51] Int. Cl.$^2$ .............................................. C10M 1/32
[52] U.S. Cl. .......................... 252/51.5 A; 252/51.5 R
[58] Field of Search ...................... 260/326.25, 326.45; 252/51.5 A, 51.5 R

[56] References Cited

U.S. PATENT DOCUMENTS

| 3,479,327 | 11/1969 | Merijan et al. | 252/51.5 R X |
| 4,049,564 | 9/1977 | Ryer et al. | 252/51.5 R X |
| 4,070,370 | 1/1978 | Elliott et al. | 252/51.5 R X |

FOREIGN PATENT DOCUMENTS 844,433  8/1960  United Kingdom ............... 252/51.5 R Primary Examiner—Delbert E. Gantz
Assistant Examiner—Andrew Metz
Attorney, Agent, or Firm—Donald L. Johnson; Robert A. Linn; Joseph D. Odenweller

[57] ABSTRACT

Polyesters suitable for use as lubricant additives are prepared by reacting a di-carboxylic acid or anhydride having a branched chain alkyl or alkenyl substituent containing at least 30 carbon atoms with a compound having the formula:

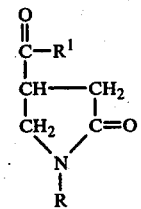

wherein R and $R^1$ are specified substituents which between them possess from 2 to 6 free hydroxyl groups. Lubricating compositions containing these polyester additives are also described.

13 Claims, No Drawings

POLYESTER LUBRICANT ADDITIVES, THEIR PREPARATION AND COMPOSITIONS CONTAINING THEM

CROSS REFERENCE TO RELATED APPLICATION

This application is a division of application Ser. No. 506,910, filed Sept. 17, 1974, and now U.S. Pat. No. 4,070,370.

The present invention relates to lubricant additives, more particularly to additives suitable for use as ashless dispersants.

According to one aspect of the present invention there is provided a polyester, prepared by reacting a di-carboxylic acid or anhydride thereof, said acid or anhydride having a branched chain alkyl or alkenyl substituent containing at least 30 carbon atoms, with a substituted carboxypyrrolidone of the following formula A such that the carboxyl groups of the acid are substantially completely esterified by hydroxyl groups of A, wherein A is:

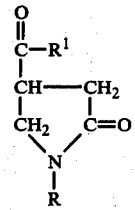

in which:

(a) R is a hydrogen atom or an alkyl, aryl, aralkyl, hydroxyalkyl, (poly)oxyalkylenealkyl or hydroxyalkylaminoalkyl group, an alkyl group substituted by one or more heterocyclic rings in which the or each heteroatom is preferably a nitrogen atom and which is free from amine —N—H groups, for example an imidazoline group or a group of the formula:

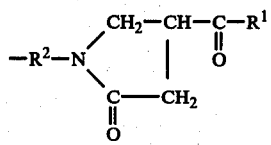

(b) each $R^1$ is a group of the formula:

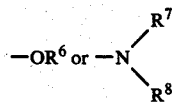

and each $R^1$ is the same as or different from any other group $R^1$;

(c) $R^2$ is an alkylene group;

(d) $R^6$ is an alkyl, (poly)oxyalkylenealkyl or hydroxyalkyl group, a group of the formula:

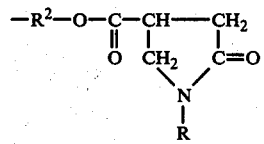

in which the groups $R^2$ and R may be the same as or different from any other group $R^2$ and R respectively, an alkyl group substituted by one or more tertiary amine groups or an alkyl group substituted by one or more heterocyclic rings in which the or each heteroatom is preferably a nitrogen atom and which is free from amine —N—H groups;

(e) $R^7$ is an alkyl, hydroxyalkyl, dialkylaminoalkyl or hydroxyalkylaminoalkyl group, or a group of the formula:

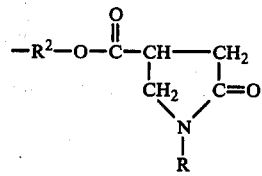

or a group of the formula:

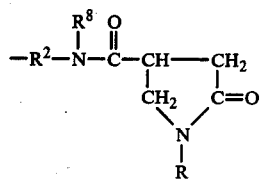

in which the groups $R^2$ and R may be the same as or different from any other group $R^2$ and R respectively, or is an alkyl group substituted by one or more heterocyclic rings in which the or each heteroatom is preferably a nitrogen atom and which is free from amine —N—H groups;

(f) $R^8$ is a hydrogen atom or as $R^7$;

(g) provided that there are a total of from 2 to 6, preferably 3 to 6, free hydroxyl groups on groups R and/or $R^1$.

In accordance with another aspect of the invention there is provided a process for preparing a polyester suitable for use as a lubricant additive which process comprises reacting a di-carboxylic acid or the anhydride thereof, said acid or anhydride having a branched chain alkyl or alkenyl substituent containing at least 30 carbon atoms, with a substituted carboxypyrrolidone of the foregoing formula A such that the carboxyl groups of the acid are substantially completely esterified by hydroxyl groups of A.

The substituted carboxypyrrolidone starting materials of foregoing formula A may be obtained using relatively simple variations of well-known techniques. Thus, it is well known that itaconic acid, or its esters, will condense with a primary amine to form a 2-pyrrolidone having a substituent on the nitrogen atom which is the residue of the amine, the 2-keto group being derived from one of the carboxyl groups of itaconic acid and having a pendant substituent derived from the other carboxyl group of itaconic acid on the carbon atom in the 4 position in the pyrrolidone ring. The pendant substituent is a carboxyl group in either free or esterified form depending on whether itaconic acid or an ester thereof has been used. To form the carboxypyrrolidone starting materials of the present invention itaconic acid, or an ester thereof, may be condensed with an aminoalcohol to yield a carboxypyrrolidone in which the substituent on the nitrogen atom has one or more free hydroxyl groups; thus monoethanolamine will form:

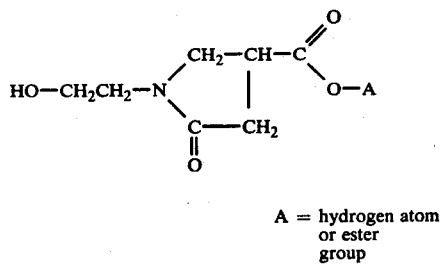

A = hydrogen atom or ester group

Similarly compounds of the formula:

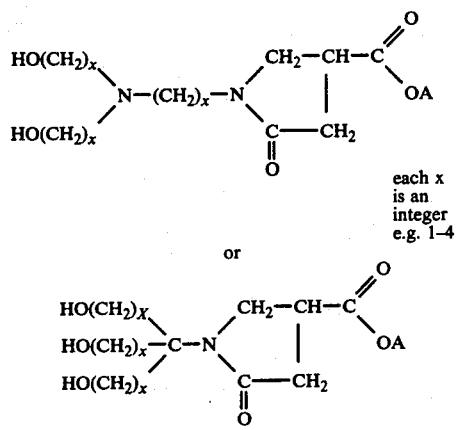

each x is an integer e.g. 1–4 may be prepared from the appropriate aminoalcohol.

Alternatively an amine other than an aminoalcohol may be used to form carboxypyrrolidones in which the substituent on the nitrogen atom does not bear a free hydroxyl group, e.g. carboxypyrrolidones of the formula:

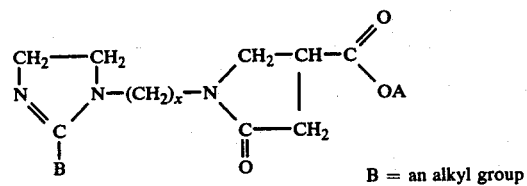

B = an alkyl group

In yet another alternative di(primary)amines may be used to form bis carboxypyrrolidones, e.g. of the formula:

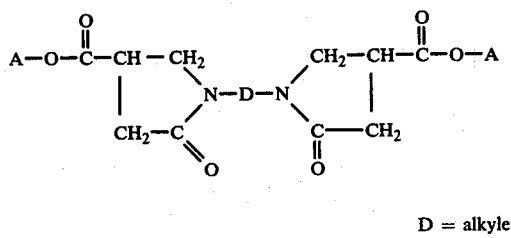

D = alkylene.

The condensation of the primary amine with the itaconic acid, or ester thereof, proceeds readily over a wide range of temperatures, e.g. up to 180° C. However, at relatively high temperatures internal esterification may occur between free hydroxyl groups on the substituent on the nitrogen atom and the pendant carboxyl group in the 4 position. Accordingly, it is preferred to carry out the condensation at a temperature of from 80° C. to 120° C. A particularly useful technique is to carry out the condensation in refluxing water.

The pendant carboxyl group on the 4 position of the carboxypyrrolidone ring may have one of a number of different forms according to the polyester final product desired. This can be achieved in a number of cases by forming the carboxypyrrolidone from an appropriately substituted ester of itaconic acid. However, it is preferred to carry out the condensation with itaconic acid or an alkyl ester thereof in which the alkyl group contains from 1 to 8, more preferably 1 to 4 carbon atoms and thereafter to convert the pendant carboxyl group to the desired form. Thus esterification of a free carboxyl group with an alcohol can be used to convert the acid form to an alkyl ester. Alternatively a carboxyl group in alkyl ester form can be transesterified to form a different alkyl ester. Similarly esterification or transesterification with a diol or polyol can be used to form a hydroxylalkyl ester of the pendant carboxyl group. Such conversion can be carried out using conventional esterification and transesterification techniques.

Alternatively, the pendant carboxyl group can be reacted with various amines to introduce nitrogen-containing substituents. For example, amidation of the pendant carboxyl group (in either free or ester form) can be used to form compounds of the formula:

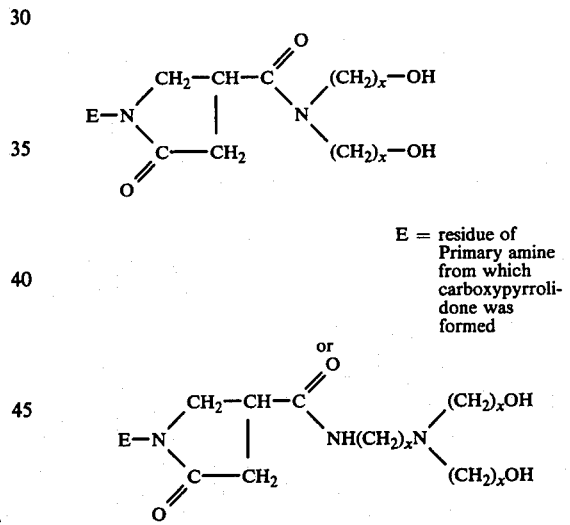

E = residue of Primary amine from which carboxypyrrolidone was formed

Amidation can usually be readily carried out by heating together the amine and carboxypyrrolidone at a temperature of from 100° to 200° C. preferably distilling out water or alcohol formed in the reaction. In most cases a temperature of from 140° to 180° C. has been found to be most suitable.

When the substituent on the pendant carboxyl group is difunctional larger quantities or carboxypyrrolidone may be used to form a bis compound, e.g. of the formula:

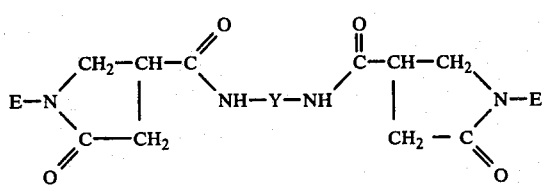

—NH—Y—NH = diamine residue

The esterification of the chosen carboxypyrrolidone starting material with the long-chain substituted carboxylic acid or anhydride in accordance with the present invention can be carried out using any of the well-known long-chain substituted dicarboxylic acids or anhydrides thereof. The long-chain substituent is preferably derived from a polyolefin, e.g. polypropylene or polybutylene, and will commonly have a molecular weight of from 700 to 3,000. The long-chain substituent confers oil solubility on the final product and the optimum size for the substituents will depend, inter alia, on the total number of substituents present in the product. Accordingly, the size of the substituent can vary widely, but normally substituents having a molecular weight of from 900 to 1500 are most preferred. It is particularly preferred to use the long-chain succinic acids derived from the reaction of a polyolefin with maleic anhydride.

The long-chain substituted acid may be reacted with the carboxypyrrolidone in an amount according to the number of free hydroxyl groups to be present. In one form of the invention a long-chain substituted dicarboxylic acid is reacted with a carboxypyrrolidone in which the substituent on the nitrogen atom has one free hydroxyl group, e.g. derived from an aminoalcohol, and the substituent on the pendant carboxyl group likewise has one free hydroxyl group to form a linear polyester comprising alternating pyrrolidone rings and long-chain substituted esterified dicarboxylic acid groups.

In another form of the invention a long-chain substituted di-carboxylic acid or anhydride is reacted with a carboxypyrrolidone in which the substituents on the nitrogen atom and on the pendant carboxyl group have a total of from 3 to 6 hydroxyl groups in such proportions that the resultant polyester contains from 1 to 4 free hydroxyl groups per long chain substituted di-carboxylic acid unit.

In a particularly preferred form of the invention a polybutenyl succinic anhydride of molecular weight from 900 to 1500 is reacted with a carboxypyrrolidone of formula A in which R is a hydroxyalkyl or hydroxyalkylaminoalkyl group, $R^1$ is —NHR$^7$ and $R^7$ is hydroxyalkyl or hydroxyalkylaminoalkyl.

The esterification may be carried out using well-known techniques. An esterification catalyst, such as p-toluene sulfonic acid is preferably used. The esterification is preferably carried out in the absence of a solvent but an inert organic solvent, particularly, a water-entraining solvent such as toluene or xylene optionally with a polar solvent such as dimethyl formamide, or mineral oil, may be used if desired.

After formation of the final products they may be purified using the usual techniques. A very useful technique is to dissolve the product in an organic solvent such as toluene or petroleum ether, water wash, filter and finally strip off the organic solvent.

The present invention, in a further aspect, also includes lubricating compositions comprising a major proportion of a lubricating oil, especially a mineral oil, having dissolved therein a minor proportion of the additives of the present invention, for example 0.1% to 10%, more preferably 0.5% to 5%, by weight based on the total weight of the composition.

The additives may also be formed into concentrates of the type commonly used by manufacturers in the blending of oil and such concentrates are also included within the scope of the present invention. In accordance with a further aspect of the invention there is provided a lubricating oil concentrate comprising a major proportion of a polyester additive of the invention and a minor proportion of a lubricating oil.

Furthermore, the additives may also be used in conjunction with additives conventionally used in lubricants, such as antioxidants, anti-wear additives, corrosion inhibitors, detergents, thickeners, load carrying agents, pour point depressants, and viscosity index improvers. They may also be formed into concentrated additive packages, of the type commonly used in oil blending, with such conventional additives. Accordingly, such additive packages and lubricants which contain such conventional additives in addition to the additives of the present invention are also within the scope of the present invention.

In accordance with a further aspect of the invention there is provided an additive package containing a minor amount of a lubricating oil and a major amount of an additive consisting of one or more polyesters of the invention in combination with one or more, conventional additives.

The present invention will now be illustrated with reference to the following examples.

EXAMPLE 1

(a) Ethanolamine (2.0 m., 122.2g) was added slowly with stirring to itaconic acid (1.0 m., 130.1g) in water (200 ml) at 80° C. The solution was refluxed for 1 hour and then stripped under vacuum (~20 mm Hg) at 190° C. The product at this stage had a total acid number (TAN) of 43.8 (0 calc). Ethanolamine (10g) was added and the mixture heated up to 200° C. Water formed in the reaction was distilled out. The acid number had dropped to 28.1. A further 30g of ethanolamine was added and the mixture heated at 190° C. for 1 hour. The mixture was finally vacuum stripped (5 mm Hg) at 240°–250° C. The product was found to contain 13.3 wt% nitrogen (13.0 wt% calc) and to have a total acid number of 4.9 and a total base number (TBN) of 36.1 (0 calc).

(b) Polyisobutene (1000 mw.) succinic anhydride (0.7m., 942.9g) was dissolved in xylene (700 ml.). To the solution was added the product of (a) (151.3g) and p-toluene sulfonic acid (1.1g.). The resultant mixture was refluxed to azeotrope off the water formed for 11 hours (10 ml. of water collected), 600 ml. of solvent was then distilled off from the reaction mixture and refluxing continued for a further 4 hours (1.2 ml. of water collected). A further 2 hour reflux produced no more water. The product was cooled, dissolved in toluene, and washed with water (200 ml.). The toluene solution was dried over anhydrous magnesium sulfate, filtered and stripped under reduced pressure to remove solvent. Paraffinic SAE 5 lubricating oil (100g.) was stirred into the product and the resultant concentrate was found to contain 1.6 wt.% nitrogen, 6.0 wt.% oxygen and to have a TAN of 2.9, a TBN of 10.1 and a saponification number of 78.3.

EXAMPLE 2

(a) N-(3-aminopropyl)-diethanolamine (0.3m., 48.7g.) was added slowly to a solution of itaconic acid (0.3m., 39.0g.) in water (80 ml.) at 80° C. The resultant solution was refluxed for 1½ hours and then stripped under vacuum (~20 mm. Hg) at 60° C. for 2 hours and 100° C./5mm. Hg. for 1 hour. The product was a very viscous yellow liquid and was found to contain 9.3 wt.% nitrogen (10.2 wt.% calc.) and to have a TAN of 187 (204.5 calc) and a TBN of 226.2 (204.5 calc).

(b) The product of (a) (68.6g.) was heated to 120° C. and N-(3-aminopropyl) diethanolamine (0.25m., 40.6g.) added in four portions distilling out any water formed after each addition. After the final addition the mixture was heated at 150°–180° C. for 2 hours and finally stripped at 210° C. under reduced pressure (4mm. Hg.). The product was found to contain 12.5 wt.% nitrogen and to have a TAN of 3.1 and a TBN of 281.

(c) A mixture of polyisobutene (1000 mw). succinic anhydride (0.18m., 242.5g.), the product of (b) (75.3g.) and a p-toluene sulfonic acid (0.3g.) was stirred and heated at 200°–220° C. in a stream of nitrogen (to remove water as it was formed) for 10 hours. The product was cooled, dissolved in toluene and washed with 1:1 water/methanol (100 ml.). The toluene solution was dried over anhydrous magnesium sulfate, filtered and stripped under reduced pressure to remove solvent. The product was found to contain 3.4 wt. % nitrogen, 6.90 wt. % oxygen; and to have a TAN of 5.9, a TBN of 82.1 and a saponification number of 61.7.

EXAMPLE 3

(a) Benzylamine (1.0 m., 107.2g) was added slowly with stirring to itaconic acid (1.0 m., 130.1g) at room temperature. The mixture was heated slowly to 170° C. and water formed during the reaction was distilled out. Heating was continued at 170° C. until no more water was evolved. The mixture was allowed to cool and then ground to a fine buff colored powder. The product was found to contain 6.4 wt. % nitrogen (6.4 wt. % calc.) and to have a TAN of 246.9 (255.8 calc.) a saponification number of 262 (255.8) and a TBN of 0 (0).

(b) The product of (a) (87.7g.) was heated with trimethylol propane oxetane (0.44 m., 51.0g.) at 200° C. for 8 hours and then stripped under vacuum (~20 mm Hg) at 220° C. The product was a viscous brown liquid and was found to contain 4.1 wt. % nitrogen and to have a TAN of 0.3, a saponification number of 159.6 and a TBN of 0.2.

(c) Polyisobutene (450 m.w.) succinic anhydride (0.3 m., 212.0 g) was dissolved in xylene (150 ml). To the solution was added the product of (b) (100.6 g) and p-toluene sulfonic acid (0.3 g). The resultant mixture was refluxed to azeotrope off the water formed for 12 hours. (3.2 ml of water collected). The solvent was then distilled off and the mixture heated at 200° C.–210° C. for 7 hours. The product was cooled, dissolved in 80/100 petroleum ether and washed with 1:1 water/methanol (100 ml). The petroleum ether solution was dried over anhydrous magnesium sulfate, filtered and stripped under reduced pressure to remove solvent. The product was a dark brown extremely viscous liquid and was found to contain 1.3 wt. % nitrogen and to have a TAN of 8.1; a TBN of 0 and a saponification number of 130.1.

EXAMPLE 4

(a) The carboxypyrrolidone was prepared in the same manner as that of Example 2 (a) from ethanolamine (5.0m. 305.5g) and itaconic acid (5.0m, 650.5g) in water (900ml). The product was found to contain 7.9 wt. % nitrogen (8.1 wt. % calc.) and to have a TAN of 292.0 (323.9 calc.), a saponification number of 398 (323.9) and a TBN of 31.8 (0).

(b) In the same manner as that of Example 2(b) the product of (a) (173.2g) was reacted with diethanolamine (1.0m., 105.1 g). The product was found to contain 10.4 wt. % nitrogen and to have a TAN of 5.6 and a TBN of 168.2.

(c) Polyisobutene (1000 mw) succinic anhydride (0.9m., 1212.3g), the product of (b) (234.3g.) mineral oil (143g, 10% w/w and p-toluene sulfonic acid (1.4g) was heated at 185°–210° C. for 9 hours and any water formed from the reaction distilled off. The product was cooled, dissolved in toluene, filtered, and washed with 1:1 water/methanol (2 × 500 ml). The toluene solution was dried over anhydrous magnesium sulfate, filtered and stripped under reduced pressure to remove solvent. The product was a dark-brown extremely viscous liquid and was found to contain 1.2 wt. % nitrogen and to have a TAN of 1.7; a TBN of 15.6 and a saponification number of 64.5.

EXAMPLE 5

(a) Aminopropyl diethanolamine (2.0 m, 324.4 g) was added slowly with stirring to dimethyl itaconate (2.0 m., 316.4g) at 60° C. The mixture was heated at 145° C. for 2 hours and methanol formed during the reaction was distilled out. The product was found to contain 10.0 wt. % nitrogen (9.7 wt. % calc.) and to have a saponification number of 203.8 (194.5 calc.), a TAN of 3.1 and a TBN of 211.2 (194.5).

(b) Polyisobutene (1000 mw) succinic anhydride (0.3 m., 404.1g) and p-toluene sulfonic acid (0.5g) were dissolved in xylene (400 mls) and the product of (a) (0.3m., 86.5g) dissolved in dimethyl formamide (100 mls). The two solutions were mixed and refluxed for 4 hours. The solvents were then distilled off and the mixture heated at 200° C. for 6 hours and any water was distilled off. The product at this stage had a TAN of 14.4. A further 14.4 g of (a) was added and heating continued for 4 hours. The product was cooled, dissolved in 80/100 petroleum ether, filtered, and washed with 1:1 water/methanol. The petroleum ether solution was dried over anhydrous magnesium sulfate, filtered and stripped under reduced pressure to remove solvent. The product was a dark brown extremely viscous liquid and was found to contain 2.0 wt. % nitrogen and to have a TAN of 8.0, a TBN of 28.9 and a saponification number of 79.6.

EXAMPLES 6 TO 26

Further products were prepared in similar manner as in the foregoing Examples and salient details of the preparation of these further products are set out in the following Tables 1 to 5. Tables 1 and 2 describe the preparation of carboxypyrrolidones from itaconic acid and dimethyl itaconate respectively. The reaction of these carboxypyrrolidones with amines and alcohols are described in Tables 3 and 4 respectively, and the preparation of polyesters of the present invention are described in Table 5. In Table 5 products 12 (c), 13 (c), 14 (c), 16 (c), 18 (c) to 24 (c) and 26 (c) were prepared by the method of Example 1 (b); products 6 (c) to 11 (c), 15 (c) and 17 (c) were prepared by the method of Example 2 (c) and product 25 (c) was prepared by the method of Example 5 (b).

Throughout the foregoing Examples 1 to 5 and in Examples 6 to 26 set out in the following Tables 1 to 5, total acid number (TAN), total base numbers (TBN) and saponification numbers are in units of mg KOH/g.

Suitability of the products of the present invention for use as ashless dispersants in lubricants was determined by MS VC and Petter AV-B Engine Tests, by Panel Coker Tests and by Spot Tests. These tests were all carried out in the manner described in U.S. Pat. No. 3,966,807, except that in the Spot Tests 3% of the test additive was mixed with the carbon black in mineral oil and the mixture was agitated for 1½ hours and then stored at 50° C. for 24 hours.

The results obtained in the MS VC tests were as follows:

| | FORMULATION A | | |
|---|---|---|---|
| Test Additive | Average Sludge (Max 10) | Average Varnish (Max 10) | Piston Skirt Varnish (Max 10) |
| Final Product of Example 1 | 8.0 | 6.1 | 6.8 |
| | FORMULATION B | | |
| Test Additive | Average Sludge (Max 10) | Average Varnish (Max 10) | Piston Skirt Varnish (Max 10) |
| Final Product of Example 4 | 7.1 | 7.4 | 7.5 |
| Final Product of Example 12 | 8.0 | 7.9 | 8.1 |

The results obtained in Petter AV-B Tests were as follows:

| | Groove Carbon (%) | | | Overall |
|---|---|---|---|---|
| Test Additive | 1st | 2nd | 3rd | Rating |
| Final Product of Example 1 | 87.0 | trace | trace | 73.0 |
| Final Product of Example 6 | 70.6 | 2.4 | nil | 62.2 |
| Final Product of Example 4 | 60.6 | 0.4 | nil | 76.1 |
| Additive X | 100.0 | 34.0 | trace | 51.0 |

Additive X is a commercially available, nitrogen containing ashless dispersant based on an ester of polybutene succinic anhydride.

The results obtained in Panel Coker and Spot Tests for products 6 to 26 are set out in the following Table 5, and results for the products of Examples 1 to 5 were as follows:

| | Panel Coker | Spot Test |
|---|---|---|
| Example 1 | 89.3 | A |
| Example 2 | 55.5 | A |
| Example 3 | 75.3 | C |
| Example 4 | 61.0 | A |
| Example 5 | 69.5 | A |

TABLE 1

| Ex. No. | AMINE | g | MOLES | ITACONIC ACID g | MOLES | REACTION Conditions | % N (calc) | TAN (calc) | SAP (calc) | TBN (calc) | YIELD % |
|---|---|---|---|---|---|---|---|---|---|---|---|
| 7(a) | AMINOPROPYL DISTHANOLAMINE | 48.7 | 0.3 | 39.0 | 0.3 | AS 2(a) | 8.5 (10.2) | 98.1 (204.5) | — | 228.1 (204.5) | 92 |
| 8(a) | 35% AXMONIA | 228.0 | 13.0 | 260.2 | 2.0 | " | 9.9 (10.9) | 351.5 (433.0) | 530.0 (435.0) | 9.4 (0) | 88 |
| 12 (a) | ETHANOLAMINE | 305.5 | 5.0 | 630.5 | 5.0 | " | 8.3 (8.1) | 254.3 (323.9) | 370.0 (323.9) | 52.4 (0) | 99 |
| 13 (a) | ANILINE | 93.1 | 1.0 | 130.1 | 1.0 | AS 3(a) | 6.3 (6.8) | 266.0 (273.4) | 273.0 (273.4) | 0 (0) | 90 |
| 14 (a) | OCTYLAMINE | 129.2 | " | " | " | " | 5.6 (5.8) | 189.4 (232.5) | 242.0 (232.5) | 0.1 (0) | 93 |
| 15 (a) | TRIS(HYDROXY-METHYL METHYL-AMINE | 121.1 | " | " | " | AS 2(a) | PREPARED IN SITU NOT ANALYSED | | | | |
| 16 (a) | AMINOPROPYL DIETHANOLAMINE | 270.0 | 1.66 | 216.0 | 1.66 | " | 10.6 (10.2) | 119.6 (204.5) | 209.2 (204.5) | 226.0 (204.5) | 78 |
| 18 (a) | ETHANOLAMINE | 122.2 | 2.0 | 260.2 | 2.0 | " | 8.1 (8.1) | 243.0 (323.9) | 353.7 (323.9) | 4.2 (0) | — |
| 21 (a) | ETHYLENE DIAMINE | 30.0 | 0.5 | 130.1 | 1.0 | AS 2(a) | 9.3 | 356.3 (394.6) | 315.1 (394.6) | (0) | 81 |
| 22 (a) | ETHANOLAMINE | 122.2 | 2.0 | 260.2 | 3.0 | AS 2(a) | 7.8 (8.1) | 240.7 (323.9) | 323.0 (323.9) | 32.6 (0) | 94 |

TABLE 2

| EXAMPLE NO. | AMINE | g | MOLES | DIMETHYL ITACONATE g | MOLES | FRACTION CONDITIONS |
|---|---|---|---|---|---|---|
| 6(a) | ETHANOLAMINE | 61.1 | 1.0 | 158.2 | 1.0 | 145° C |
| 9(a) | CASAMINE C | 53.4 | 0.2 | 1.6 | 0.2 | 150° C |
| 10 | TRIS(HYDROXY METHYL) METHYLAMINE | 60.6 | 0.5 | 79.1 | 0.5 | 160° C |
| 11 (a) | ETHANOLAMINE | 152.8 | 2.5 | 395.4 | 2.5 | 145° C |
| 17 (a) | " | 183.3 | 3.0 | 474.6 | 3.0 | 160° C |
| 19 (a) | " | " | " | " | " | " |
| 20 (a) | *POLYGLYCOLAMINE H 163 | 163.0 | 1.0 | 158.2 | 1.0 | " |
| 23 (a) | 2-AMINO-2-METHYL 1,3-PROPANE DIOL | 315.3 | 3.0 | 474.6 | 3.0 | " |

| EXAMPLE NO | % N (CALC) | TAN (CALC) | SAP (CALC) | TBN (CALC) | YIELD % |
|---|---|---|---|---|---|
| 5(a) | 7.6 (7.5) | 1.1 (0) | 325.0 (299.5) | 6.3 (0) | 95 |
| 9(a) | 9.8 | 48.5 | 126.0 | 134.2 | 94 |

TABLE 2-continued

|  | (10.7) | (0) | (142.7) | (142.7) |  |
|---|---|---|---|---|---|
| 10 | 6.4 | 2.6 | 272.0 | 48.0 | 79 |
| (a) | (5.7) | (0) | (226.8) | (0) |  |
| 11 | 8.0 | 1.8 | 311.0 | 8.7 | 93 |
| (a) | (7.5) | (0) | (299.5) | (0) |  |
| 17 | 7.4 | 1.6 | 281.4 | 2.7 | 83 |
| (a) | (7.5) | (0) | (299.5) | (0) |  |
| 19 | 7.6 | 1.8 | 304.0 | 1.8 | 96 |
| (a) | (7.5) | (0) | (299.5) | (0) |  |
| 20 | 5.0 | 5.3 | 206.0 | 7.7 | 82 |
| (a) | (4.8) | (0) | (194.0) | (0) |  |
| 23 | 6.0 | 12.0 | 278.3 | 49.4 | 98 |
| (a) | (6.1) | (0) | (242.5) | (0) |  |

PREPARATIVE METHOD FOR ALL PRODUCTS AS FOR EXAMPLE 5 (a)
*Aminoethyl-2-undecylimidazoline ex Casa Chemicals
**O-hydroxyethoxyethylpropanolamine ex Union Carbide

TABLE 3

| EXAMPLE NO | CARBOXY PYRROLIDONE DERIVED FROM | g | MOLES | AMINE | g | MOLES |
|---|---|---|---|---|---|---|
| 6(b) | 6(a) | 112.4 | 0.6 | PROPANE DIAMINE | 22.2 | 0.3 |
| 7(b) | 7(a) | 55.8 | 0.2 | OCTYLAMINE | 31.0 | 0.24 |
| 8(b) | 8(a) | 47.0 | 0.3 | AMINOPROPYL-DIETHANOLAMINE | 48.7 | 0.3 |
| 9(b) | 9(a) | 39.3 | 0.1 | DIETHANOLAMINE | 10.5 | 0.1 |
| 10(b) | 10(a) | 54.9 | 0.2 | AMINOPROPYL-DIETHANOLAMINE | 32.5 | 0.2 |
| 11(b) | 11(a) | 187.3 | 1.0 | " | 162.3 | 1.0 |
| 12(b) | 12(a) | 346.4 | 2.0 | AMINOETHYL-ETHANOLAMINE | 104.0 | 1.0 |
| 13(b) | 12(a) | 86.6 | 0.5 | ETHYLENE DIAMINE | 15.0 | 0.25 |
| 14(b) | 13(a) | 82.1 | 0.4 | AMINOPROPYL-DIETHANOLAMINE | 64.9 | 0.4 |

| EXAMPLE NO | % N | TBN | TAN | YIELD % |
|---|---|---|---|---|
| 6(b) | 14.3 | 59.4 | 29.8 | 91 |
| 7(b) | 10.9 | 169.0 | 3.4 | 86 |
| 8(b) | 12.6 | 193.0 | 6.8 | 81 |
| 9(b) | 9.8 | 157.6 | 6.4 | 93 |
| 10(b) | 10.7 | 211.0 | 7.0 | 91 |
| 11(b) | 13.4 | 258.0 | 2.8 | 95 |
| 12(b) | 12.0 | 70.1 | 14.4 | 92 |
| 13(b) | 14.3 | 40.0 | 4.9 | 90 |
| 14(b) | 12.1 | 202.0 | 6.0 | 92 |

| EXAMPLE NO | CARBOXY PYRROLIDONE DERIVED FROM | g | MOLES | AMINE | g | MOLES |
|---|---|---|---|---|---|---|
| 15(b) | 14(a) | 120.7 | 0.5 | AMINOPROPYL-DIETHANOLAMINE | 81.1 | 0.5 |
| 16(b) | 15(a) | 233.2 | 1.0 | TRIS(HYDROXY-METHYL)METHYL-AMINE | 121.1 | 1.0 |
| 17(b) | 16(a) | 109.7 | 0.4 | DIETHYLAMINO PROPYLAMINE | 44.9 | 0.44 |
| 19(b) | 18(a) | 86.6 | 0.5 | ETHANOLAMINE | 30.6 | 0.5 |
| 21(b) | 20(a) | 202.4 | 0.7 | AMINOPROPYL-DIETHANOLAMINE | 113.5 | 0.7 |
| 22(b) | 21(a) | 113.7 | 0.4 | ETHANOLAMINE | 48.8 | 0.8 |

| EXAMPLE NO | % N | TBN | TAN | YIELD % |
|---|---|---|---|---|
| 15(b) | 10.6 | 159.6 | 3.7 | 80 |
| 16(b) | 8.6 | — | — | — |
| 17(b) | 15.3 | 303.2 | 14.4 | 86 |
| 19(b) | 12.3 | 23.1 | 3.5 | 84 |
| 21(b) | 10.1 | 166.9 | 2.0 | 85 |
| 22(b) | 15.0 | 21.4 | 2.6 | 84 |

TABLE 4

| EXAMPLE NO. | CARBOXY PYRROLIDONE DERIVED FROM | g | MOLES | ALCOHOL | g | MOLES |
|---|---|---|---|---|---|---|
| 18(b) | 17(a) | 93.7 | 0.5 | *ETHODUOMEEN T13 | 204.0 | 0.5 |
| 20(b) | 19(a) | " | " | TRIETHANOL-AMINE | 74.6 | 0.5 |
| 23(b) | 22(a) | 86.6 | " | ETHANOLAMINE | 15.3 | 0.25 |
| 24(b) | 23(a) | 162.0 | 0.7 | PROPANE 1,3-DIOL | 26.7 | 0.35 |

| EXAMPLE NO | CATALYST | % N | SAP | TBN | TAN | YIELD % |
|---|---|---|---|---|---|---|

TABLE 4-continued

| | | | | | | |
|---|---|---|---|---|---|---|
| 18(b) | SODIUM METHOXIDE 0.1g | 5.9 | 102.2 | 132.5 | 7.0 | 86 |
| 20(b) | SODIUM METHOXIDE 0.1g | 9.4 | 160.5 | 160.1 | 5.2 | 88 |
| 23(b) | PTS A 0.1g | 11.5 | 272.0 | — | — | 89 |
| 24(b) | SODIUM METHOXIDE 0.1g | 5.9 | 187.4 | 72.0 | 3.9 | 81 |

*N-alkylpropylenediamine derived from tallow ethoxylated with 3 moles ethylene oxide ex Armour Hess.

TABLE 5

| EXAMPLE NO | HYDROXY COMPOUND DERIVED FROM | g | PIBSA PIB MW | g |
|---|---|---|---|---|
| 6(c) | 6(b) | 96.2 | 1000 | 336.7 |
| 7(c) | 7(b) | 38.5 | " | 134.7 |
| 8(c) | 8(b) | 30.1 | " | " |
| 9(c) | 8(b) | 42.3 | " | 272.3 |
| 10(c) | 9(b) | 23.3 | " | 67.3 |
| 11(c) | 10(b) | 20.2 | " | " |
| *12(c) | 11(b) | 276.5 | " | 1172.6 |
| 13(c) | 12(b) | 41.4 | " | 134.7 |
| 14(c) | 13(b) | 37.0 | " | " |
| 15(c) | 14(b) | 69.8 | 650 | 111.8 |
| 16(c) | 15(b) | 96.4 | 1500 | 418.6 |

*10% W/W MINERAL OIL ADDED TO FINAL PRODUCT

| EXAMPLE NO | % N | TBN | SAP | TAN | YIELD % | PANEL COKER TEST RESULT | SPOT TEST RATING |
|---|---|---|---|---|---|---|---|
| 6(c) | 2.1 | 0.7 | 64.7 | 2.6 | 82 | 85.8 | A |
| 7(c) | 2.7 | 30.5 | 54.5 | 3.2 | 96 | 67.8 | A |
| 8(c) | 2.3 | 34.5 | 72.1 | 5.6 | 79 | 57.0 | A |
| 9(c) | 2.3 | 43.1 | 59.2 | 2.4 | 91 | 69.0 | A |
| 10(c) | 2.5 | 11.5 | 65.3 | 3.8 | 87 | 75.5 | A |
| 11(c) | 2.4 | 51.2 | 57.7 | 2.9 | 84 | 81.0 | A |
| *12(c) | 2.4 | 50.4 | 62.4 | 5.0 | — | 64.5 | A |
| 13(c) | 3.0 | 14.8 | 79.7 | 7.9 | 86 | 63.8 | A |
| 14(c) | 3.0 | 2.5 | 63.3 | 2.6 | 82 | 87.0 | A |
| 15(c) | 4.6 | 54.2 | 62.2 | 10.0 | 75 | — | — |
| 16(c) | 1.9 | 26.0 | 45.1 | 4.8 | 80 | 66.8 | A/B |

*10% W/W MINERAL OIL ADDED TO FINAL PRODUCT

| EXAMPLE NO | HYDROXY COMPOUND DERIVED FROM | g | PIBSA PIB MW | g |
|---|---|---|---|---|
| 17(c) | 16(b) | 131.0 | 1000 | 404.1 |
| 18(c) | 17(b) | 107.5 | " | " |
| 19(c) | 15(b) | 38.5 | *840 | 123.8 |
| 20(c) | 18(b) | 169.0 | 1000 | 410.4 |
| 21(c) | 19(b) | 21.6 | 1900 | 374.0 |
| 22(c) | 20(b) | 61.0 | 1300 | 412.6 |
| 23(c) | 21(b) | 125.8 | 1500 | 502.4 |
| 24(c) | 22(b) | 37.0 | 1900 | 374.0 |
| 25(c) | 23(b) | 37.2 | 1500 | 167.5 |
| 26(c) | 24(b) | 79.1 | 1000 | 269.4 |

*derived from propylene

| EXAMPLE NO | % N | TBN | SAP | TAN | YIELD % | PANEL COKER TEST RESULT | SPOT TEST RATING |
|---|---|---|---|---|---|---|---|
| 17(c) | 1.2 | 16.6 | 58.6 | 4.4 | 75 | 91.8 | A |
| 18(c) | 2.1 | 31.9 | 53.7 | 8.5 | 65 | 68.8 | A |
| 19(c) | 2.3 | 38.9 | 58.3 | 6.8 | 63 | 84.8 | B |
| 20(c) | 1.6 | 39.0 | 66.4 | 3.2 | 85 | 77.0 | B |
| 21(c) | 0.6 | 0.3 | 30.5 | 4.6 | 67 | 88.3 | A |
| 22(c) | 0.7 | 17.8 | 46.8 | 3.1 | 63 | 83.5 | A |
| 23(c) | 1.7 | 30.3 | 53.6 | 4.3 | 70 | 66.3 | A |
| 24(c) | 0.9 | 1.7 | 39.4 | 5.5 | 72 | 88.5 | A |
| 25(c) | 1.1 | 2.2 | 46.9 | 6.1 | 83 | 76.3 | B |
| 26(c) | 1.1 | 12.5 | 88.8 | 3.2 | 60 | 87.8 | A |

We claim:

1. A lubricating composition comprising a major amount of lubricating oil and a minor amount sufficient to impart dispersant properties to said oil of a polyester additive which is the product of the reaction at elevated temperature from reflux up to about 210° C. with removal of water of a polyolefin substituted succinic acid or anhydride wherein said polyolefin substituent has a molecular weight of about 700–3,000 with a substituted carboxypyrrolidone of the following formula A

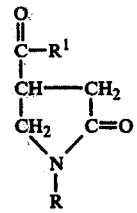

in which (a) R is selected from the group consisting of a hydrogen atom, an alkyl containing up to 8 carbon atoms, a phenyl group, a benzyl group, a hydroxyalkyl group containing 1-3 hydroxy radicals, a polyoxyalkylenealkyl group containing up to an average of about 2 oxyalkylene groups, a hydroxyalkylaminoalkyl group, a carboxypyrrolidone substituted $C_{2-6}$ alkyl group, and an imidazoline substituted $C_{1-4}$ alkyl group, (b) each $R^1$ is independently selected from a group consisting of

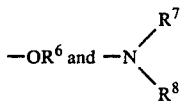

(c) $R^6$ is selected from the group consisting of alkyl groups containing up to 8 carbon atoms, polyoxyalkylene alkyl groups containing up to an average of about 2 oxyalkylene groups, hydroxyalkyl groups containing 1-3 hydroxy radicals, imidazoline substituted $C_{1-4}$ alkyl groups, and groups having the formula

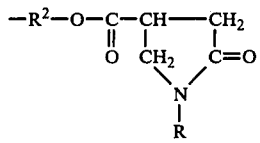

in which the groups R and $R^2$ independently are as herein defined, (d) $R^2$ is alkylene containing 2-6 carbon atoms, (e) $R^7$ is selected from the group consisting of alkyl groups containing up to 8 carbon atoms, hydroxyalkyl groups containing 1-3 hydroxy radicals, dialkylaminoalkyl groups, hydroxyalkylaminoalkyl groups, imidazoline substituted $C_{1-4}$ alkyl groups, groups having the formula

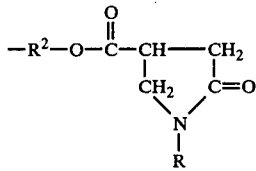

and groups having the formula

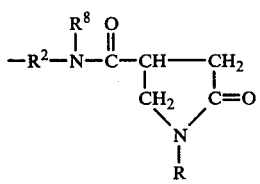

in which the groups R and $R^2$ independently are as herein defined, (f) $R^8$ is selected from the group consisting of hydrogen, alkyl groups containing up to 8 carbon atoms, hydroxyalkyl groups containing up to 3 hydroxy groups, dialkyl aminoalkyl groups, imidazoline substituted $C_{1-4}$ alkyl groups, hydroxyalkylaminoalkyl groups and groups having the formula

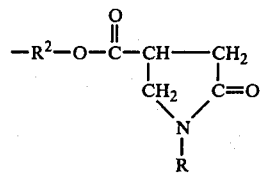

in which the groups R and $R^2$ independently are as herein defined and (g) provided that there are a total of from 2-6 free hydroxy groups on groups R and or $R^1$.

2. A lubricating composition of claim 1 wherein at least one of R, $R^6$ and $R^7$ and $R^8$ is a $C_{1-4}$ alkyl group substituted by at least one imidazoline group.

3. A lubricating composition of claim 1 wherein there are a total of from 3 to 6 free hydroxyl groups on groups R and/or $R^1$.

4. A lubricating composition of claim 1 wherein said polyolefin substituent of said succinic acid or anhydride thereof is derived from polybutene.

5. A lubricating composition of claim 4 wherein said polyolefin substituent has a molecular weight of from 900 to 1500.

6. A lubricating composition of claim 1 wherein (a) the substituents on the nitrogen atom and on the pendant carboxyl group of the substituted carboxypyrrolidone together have a total of from 3 to 6 hydroxyl groups; and (b) the substituted carboxypyrrolidone is reacted with said polyolefin substituted succinic acid or ahydride thereof in an amount to provide a polyester containing from 1 to 4 free hydroxyl groups per succinic acid unit.

7. A lubricating composition of claim 1 wherein said polyester additive is the product of the reaction of a polybutenyl succinic anhydride in which the polybutenyl substituent has a molecular weight of from 900 to 1500, and a substituted carboxypyrrolidone of formula A in which R is selected from the group consisting of said hydroxyalkyl group and said hydroxyalkylaminoalkyl group, $R^1$ is —$NHR^7$ and $R^7$ is selected from the group consisting of said hydroxyalkyl group and said hydroxyalkylaminoalkyl group.

8. A lubricating composition of claim 1 wherein said polyester additive is the product of the reaction of a polybutenyl-substituted succinic acid or anhydride with a substituted carboxypyrrolidone of formula A, in which R is a hydroxyalkyl group and $R^1$ is the group

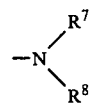

in which $R^7$ is a hydroxyalkylaminoalkyl group and $R^8$ is hydrogen.

9. A lubricating composition of claim 8 wherein R is a hydroxyethyl group and $R^7$ is N,N-di-hydroxyethyl-3-aminopropyl.

10. A lubricating composition comprising a major amount of lubricating oil and a minor amount sufficient to impart dispersant properties of a polyester additive made by the process comprising reacting at elevated temperature of about 80°-180° C. a hydroxyamine compound selected from the group consisting of monohydroxyalkyl amines and di-hydroxyalkyl aminoalkyl amines with itaconic acid or alkyl esters thereof to form an intermediate carboxypyrrolidone compound and reacting said intermediate at elevated temperature from reflux up to about 210° C. with removal of water with a polyolefin substituted succinic acid or anhydride, said polyolefin substituent having a molecular weight of about 700–3,000.

11. A lubricating composition of claim 10 wherein said hydroxyalkyl amine is monoethanol amine and said di-hydroxyalkyl aminoalkyl amine is 3-aminopropyl diethanol amine.

12. A lubricating composition of claim 10 wherein said itaconic acid or ester is first reacted with said monohyroxyalkyl amine and then reacted with said di-hydroxyalkyl aminoalkyl amine to form said carboxypyrrolidone intermediate which is reacted with said polyolefin-substituted succinic acid or anhydride.

13. A lubricating composition of claim 12 wherein said monohydroxyalkyl amine is monoethanol amine and said dihydroxyalkyl aminoalkyl amine is 3-aminopropyl diethanol amine.

* * * * *

UNITED STATES PATENT AND TRADEMARK OFFICE
CERTIFICATE OF CORRECTION

PATENT NO. : U. S. 4,127,493
DATED : November 28, 1978
INVENTOR(S) : John S. Elliott et al It is certified that error appears in the above-identified patent and that said Letters Patent are hereby corrected as shown below:

Cover page: "(73) Assignee: Ethyl Corporation, Richmond, Va." should be
-- (73) Assignee: Edwin Cooper and Company Limited, Bracknell, England --

Table 1, spanning Columns 9 and 10 - Example 8(a) under heading "Amine" - 35% Axmonia" should be
-- 35% Ammonia --

Table 1, spanning Columns 9 and 10 - Example 12(a) under heading "Itaconic Acid," subheading "g" - "630.5" should be -- 650.5 --

Table 1, spanning Columns 9 and 10 - Example 22(a) under heading "Itaconic Acid," subheading "moles" - "3.0" should be -- 2.0 --

Table 2, spanning Columns 9 and 10 - under heading "Example No." - "5(a)" should be -- 6(a) --

Table 5, spanning Columns 13 and 14 - Example 19(c) under heading "TBN" - "38.9" should be -- 32.9 --

UNITED STATES PATENT AND TRADEMARK OFFICE
CERTIFICATE OF CORRECTION

PATENT NO. : U. S. 4,127,493
DATED : November 28, 1978
INVENTOR(S) : John S. Elliott et al It is certified that error appears in the above–identified patent and that said Letters Patent are hereby corrected as shown below:

Claim 1, Column 15 - subletter "(c)" should be -- (d) --

- subletter "(d)" should be -- (c) --

Signed and Sealed this

Fifteenth Day of May 1979

[SEAL]

Attest:

RUTH C. MASON
Attesting Officer

DONALD W. BANNER
Commissioner of Patents and Trademarks